United States Patent
Axén et al.

(10) Patent No.: US 12,365,862 B2
(45) Date of Patent: Jul. 22, 2025

(54) METHOD FOR CONTROL OF A BIOPROCESS

(71) Applicant: Cytiva Sweden AB, Uppsala (SE)

(72) Inventors: Andreas Axén, Uppsala (SE); Helena Ohrvik, Uppsala (SE); Martin Antti, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 1058 days.

(21) Appl. No.: 17/294,716

(22) PCT Filed: Dec. 3, 2019

(86) PCT No.: PCT/EP2019/083528
§ 371 (c)(1),
(2) Date: May 18, 2021

(87) PCT Pub. No.: WO2020/120232
PCT Pub. Date: Jun. 18, 2020

(65) Prior Publication Data
US 2022/0010261 A1     Jan. 13, 2022

(30) Foreign Application Priority Data
Dec. 13, 2018    (GB) ..................... 1820282

(51) Int. Cl.
*C12M 3/00*    (2006.01)
*C12M 1/34*    (2006.01)
(Continued)

(52) U.S. Cl.
CPC ............ *C12M 41/48* (2013.01); *C12M 41/34* (2013.01); *C12M 41/44* (2013.01); *C12M 41/46* (2013.01);
(Continued)

(58) Field of Classification Search
CPC ....... C12M 41/34; C12M 41/36; C12M 41/48
See application file for complete search history.

(56) References Cited

U.S. PATENT DOCUMENTS

| 2017/0130186 A1* | 5/2017 | Berry ................. C12M 41/48 |
| 2017/0138924 A1 | 5/2017 | Beighley |
| 2019/0137338 A1* | 5/2019 | Webster ............. C12M 41/48 |

FOREIGN PATENT DOCUMENTS

| CN | 104081296 A | 10/2014 |
| CN | 106575102 A | 4/2017 |

(Continued)

OTHER PUBLICATIONS

PCT International Search Report and Written Opinion for PCT/EP2019/083528 mailed Feb. 25, 2020 (8 pages).
(Continued)

*Primary Examiner* — Nathan A Bowers
(74) *Attorney, Agent, or Firm* — Eversheds-Sutherland (US) LLP

(57) ABSTRACT

The present invention relates to a computer implemented method (400) performed by a controller (C) configured to control a bioprocess comprised in a bioreactor (BR), the method comprising obtaining (410) measurement results by performing spectrophotometry of a bioprocessing fluid (FL), generating (420) control parameters based on the measurement results and one model and, controlling (430) the bioprocess using the generated parameters.

15 Claims, 4 Drawing Sheets

(51) Int. Cl.
*C12M 1/36* (2006.01)
*G05B 19/00* (2006.01)
*G05B 19/4155* (2006.01)

(52) U.S. Cl.
CPC ......... *G05B 19/4155* (2013.01); *C12M 41/36* (2013.01); *G05B 2219/32287* (2013.01)

(56) References Cited

FOREIGN PATENT DOCUMENTS

| | | |
|---|---|---|
| CN | 106896800 A | 6/2017 |
| WO | 2001/06233 A1 | 1/2001 |
| WO | 2014/144999 A1 | 9/2014 |
| WO | 2016/004322 A2 | 1/2016 |
| WO | 2019/071076 A1 | 4/2019 |
| WO | 2019/079165 A1 | 4/2019 |

OTHER PUBLICATIONS

Great Britain Search Report for GB Application No. 1820282.0 mailed May 31, 2019 (7 pages).
Chinese Office Action and Search Report for 201980082425.2, mailed Feb. 27, 2024 (14 pages).

* cited by examiner

METHOD FOR CONTROL OF A BIOPROCESS

CROSS REFERENCE TO RELATED APPLICATIONS

This application claims the priority benefit of PCT/EP2019/083528, filed on Dec. 3, 2019, which claims the benefit of Great Britain Application No. 1820282.0, filed on Dec. 13, 2018, the entire contents of which are incorporated by reference herein.

TECHNICAL FIELD

The present invention relates to a method for controlling a bioprocess. The invention further relates to a controller and a system.

BACKGROUND

The biotechnology industry frequently uses bioreactors for performing a bioprocess such as cultivation of cells. Performing a bioprocess typically involves controlling flow of one or more additive fluids and/or one or more additive gases to a bioprocessing fluid. An example of an additive fluid may be glucose. An example of an additive gas may be oxygen.

In one example, during a typical bioprocessing manufacturing process, there is typically a need to monitor process properties/bioprocessing variables in the bioprocessing fluid. For example, the process properties/variables that need to be monitored may include glucose content, lactose/lactate content, viable cell content temperature, fluid pressure, fluid pH, fluid conductivity, and the like.

A problem with controlling bioprocesses is that the nature of the monitored process properties/bioprocessing variables and/or the nature of the bioprocess may prevent the use of sensors in the bioprocessing fluid, e.g. when the bioprocess involves cell cultivation.

In conventional setups, samples of the bioprocessing fluid are periodically taken and analyzed outside of the bioreactor to determine process properties/bioprocessing variables in the bioprocessing fluid. This has the drawback of being a complex and work intensive activity requiring an operator present to generate the samples.

Some conventional solutions determine a model for predicting the process properties/bioprocessing variables.

One example is shown in "Orthogonal projection to latent structures solution properties for chemometrics and systems biology data", David J. Biagionia, David P. Astling, Peter Graf and Mark F. Davis, Journal of chemometrics DOI: 10.1002/cem.1398.

A further example is described in "In Situ Monitoring of CHO Cell Culture Medium Using Near-Infrared Spectroscopy", Robert A. Mattes, Denise Root, David Chang, Mike Molony, and Mahalia Ong, BioProcess International, January 2007.

A further example is shown in "In Situ Infrared Spectroscopy as a PAT Tool of Great Promise for Real-Time Monitoring of Animal Cell Culture Processes", Li M, Ebel B, Courtes F, Guedon E and Marc A, Austin Journal of Analytical and Pharmaceutical Chemistry, May 20, 2016.

A further example is shown in "Orthogonal projections to latent structures (O-PLS)", Johan Trygg and Svante Vold, Journal of Chemometrics, 16:118-128, 18 Jan. 2002, https://doi.org/10.1002/cem.695.

A further problem is that a flow of the one or more additive fluids and/or the one or more additive gases to the bioprocessing fluid need to be controlled dependent on the process properties/bioprocessing variables in the bioprocessing fluid.

A further problem is that the behavior of the bioprocess changes over time, e.g. requiring a faster response to changes in the process properties/bioprocessing variables when controlling the flow of the one or more additive fluids and/or the one or more additive gases to the bioprocessing fluid.

Some conventional solutions, e.g. as described in the examples above, have used evaluation models for spectroscopic data collected from a large reference set of bioprocessing conditions, where the manually determined process properties/bioprocessing variables are correlated with corresponding spectroscopic data from readings obtained from sensors in the bioprocessing fluid. This has the drawback of needing the generation of extensive data sets that models can be based on. A further drawback is that the generated model is commonly, with acceptable accuracy, only applicable to the very bioprocess scale and bioreactor system in which the data set was generated. A further drawback is that the generated model is commonly, with acceptable accuracy, only applicable to a particular time interval or phase of the bioprocess. Thus, multiple models are required to obtain process properties/bioprocessing variables during the entire duration of the bioprocess.

There is therefore a need for an improved method for controlling a bioprocess.

OBJECTS OF THE INVENTION

An objective of embodiments of the present invention is to provide a solution which mitigates or solves the drawbacks and problems described above.

SUMMARY OF THE INVENTION

The above objective is achieved by the subject matter described herein. Further advantageous implementation forms of the invention are further defined herein According to a first aspect of the invention, the above mentioned and other objectives are achieved by a computer implemented method performed by a controller configured to control a bioprocess comprised in a bioreactor, the method comprising obtaining measurement results by performing spectrophotometry of a bioprocessing fluid, generating control parameters based on the measurement results and one model and, controlling the bioprocess using the generated parameters.

An advantage of the embodiment according to the first aspect is that improved control of a bioprocess is obtained. A further advantage is that computational complexity is reduced and ranges of operational bioprocessing conditions are increased as one single model is used for the entire duration of a bioprocess.

According to a second aspect of the invention, the above mentioned and other objectives are achieved by a controller, the controller comprising processing circuitry and a memory, said memory containing instructions executable by said processor, whereby said controller is operative to perform any of the method steps according to the first aspect.

According to a third aspect of the invention, the above mentioned and other objectives are achieved by a bioprocessing system comprising a sensor configured to perform spectrophotometry of a bioprocessing fluid and provide measurement results comprised in a control signal, a first controllable flow unit configured to control a flow of one or more additive gases to a bioreactor in response to control signals, a second controllable flow unit configured to control a flow of one or more additive fluids to a bioreactor in response to control signals and the controller according to the second aspect further configured to receive/send control signals to/from the sensor, the first controllable flow unit and the second controllable flow unit.

According to a fourth aspect of the invention, the above mentioned and other objectives are achieved by a computer program comprising computer-executable instructions for causing a controller, when the computer-executable instructions are executed on processing circuitry comprised in the controller, to perform any of the method steps according to the first aspect.

According to a fifth aspect of the invention, the above mentioned and other objectives are achieved by a computer program product comprising a computer-readable storage medium, the computer-readable storage medium having the computer program according to the fourth aspect embodied therein.

The advantages of the second, third, fourth and fifth aspect of the invention are at least the same as for the first aspect.

Further applications and advantages of embodiments of the invention will be apparent from the following detailed description.

Figure 1:
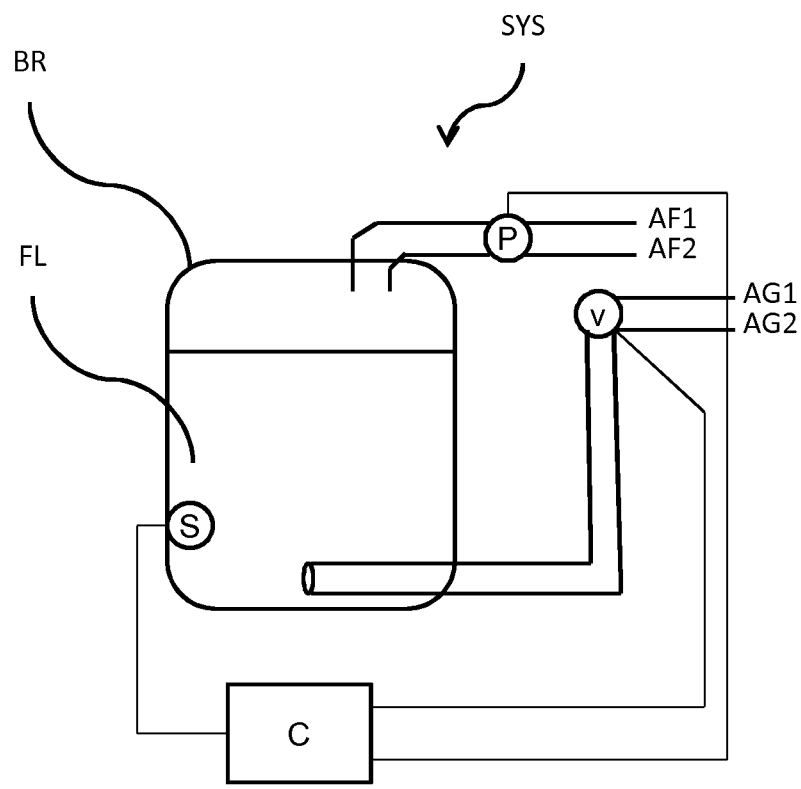
FIG. 1 shows a bioprocessing system according to one or more embodiments of the present disclosure.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

DETAILED DESCRIPTION

An "or" in this description and the corresponding claims is to be understood as a mathematical OR which covers "and" and "or", and is not to be understood as an XOR (exclusive OR). The indefinite article "a" in this disclosure and claims is not limited to "one" and can also be understood as "one or more", i.e., plural.

In this disclosure, the term "phase" or "bioprocess phase" denotes distinguishable phases in a bioprocess. In an example of a cell cultivation bioprocess, the phases may be a lag phase, a log phase or logarithmic phase and a stationary phase. Cells in culture usually proliferate following a standard growth pattern. The first phase of growth after the culture is seeded is the lag phase, which is a period of slow growth when the cells are adapting to the culture environment and preparing for fast growth. The lag phase is followed by the log phase (i.e., "logarithmic" phase), a period where the cells proliferate exponentially and consume the nutrients in the growth medium. When all of the growth medium, such as glucose, is spent, the bioprocess enters the stationary phase (i.e., plateau phase), where the proliferation of cells is greatly reduced or ceases entirely. Typically this occurs when the nutrients in a bioprocessing fluid are depleted or when the cells occupy all of an available substrate. The bioprocess can e.g. be a process of cell cultivation, such as cultivation of mammalian cells, e.g. chinese hamster ovary (CHO) cells.

In this disclosure, the terms wanted/unwanted bioprocessing variables denotes properties of a bioprocess obtainable from measurement results, e.g. in the form of a near infrared (NIR) absorption spectrum. A subset of the bioprocessing variables may be classified as wanted variables and another set may be classified as unwanted bioprocessing variables interfering with the wanted bioprocessing variables. Examples of a wanted variable may be any selection of any of glucose content, lactate content and viable cell density. An example of an unwanted variable may be gassing or additive gas flow rate/content, bioprocessing time, ambient air temperature and temperature of the bioprocessing fluid FL.

FIG. 1 shows a bioprocessing system SYS according to one or more embodiments of the present disclosure. The bioprocessing system SYS comprises a sensor S configured to perform spectrophotometry of a bioprocessing fluid FL and provide measurement results comprised in a control signal. The sensor S may e.g. be a probe designed for to be in direct contact with the bioprocess fluid and/or configured to generate an absorbance spectrum in the NIR wave length region. Alternatively or additionally the probe may e.g. be a probe designed to be in direct contact with the bioprocess fluid and/or configured to generate a Raman spectrum, e.g. a spectrophotometry sensor, as commercially available from Hellma GmbH & Co. (Germany).

Figure 3:
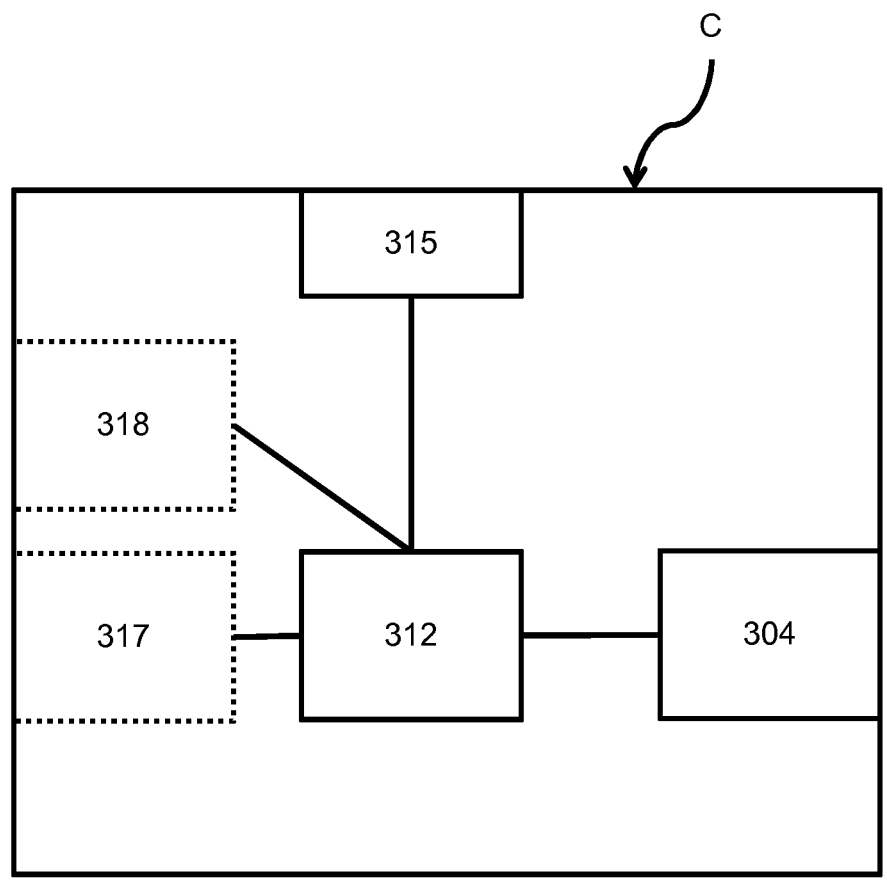
FIG. 3 shows the controller according to one or more embodiments of the present disclosure.

The bioprocessing system SYS further comprises a controller C, further described in relation to FIG. 3. The bioprocessing system SYS further comprises a first controllable flow unit V configured to control a flow of one or more additive gases AG1-AG2 to a bioreactor BR in response to received control signals. The first controllable flow unit V may e.g. comprise one or more electrically controlled valve units configured to control the flow of one or more additive gases AG1-AG2 to a bioreactor BR by, at least partially, opening/closing one or more valves in response to the control signals. The gases may e.g. be oxygen $O_2$ and/or carbon dioxide $CO_2$. The bioprocessing system SYS further comprises a second controllable flow unit P configured to control a flow of one or more additive fluids AF1-AF2 to a bioreactor BR in response to control signals. The second controllable flow unit P may e.g. comprise one or more pumps and or one or more valve units. The one or more additive fluids AF1-AF2 may e.g. comprise any one of glucose, lactose/lactate, amino acids, carbohydrates, vitamins, minerals, growth factors or hormones.

The controller C is communicatively coupled to the sensor S, the first controllable flow unit V and the second controllable flow unit P. The controller is further configured to receive/send control signals to/from the sensor S, the first controllable flow unit V and the second controllable flow unit P.

The bioprocessing system SYS may further optionally be coupled to a bioreactor BR, as shown in FIG. 1. The first controllable flow unit V and the second controllable flow unit P may be couplable to one or more inlets of the bioreactor BR, thereby allowing the one or more additive gases AG1-AG2 and/or the one or more additive fluids AF1-AF2 to mix into the bioprocessing fluid FL. The sensor S may be configured to be comprised in the bioreactor BR or configured to be inserted into the bioreactor BR such that the sensor S is at least in part in contact with the bioprocessing fluid FL. The bioreactor BR can e.g. comprise a single-use flexible bag as a bioreactor vessel, either supported in a rigid support vessel (as exemplified by an Xcellerex' XDR bioreactor, GE Healthcare Life Sciences) or placed on a rocking platform (as exemplified by a WAVE™ bioreactor, GE Healthcare Life Sciences).

In one example, the controller C comprises one single model, used to generate and/or predict values of bioprocessing properties/bioprocessing variables. The controller C obtains/receives measurement results in a control signal from the sensor S, e.g. a NIR spectrum/spectra. The measurement results are obtained by the sensor S by performing spectrophotometry of the bioprocessing fluid FL comprised in the bioreactor BR. The controller C then inputs the measurement results into the model to generate/predict control parameters based on the measurement results and the one model. The generated control parameters may e.g. define how much the flow of the one or more additive gases AG1-AG2 or the flow of the one or more additive fluids AF1-AF2 should be adapted in response to the measurement results. The controller C may further be configured to control the bioprocess using the generated parameters. In one example, the generated control parameters comprises proportional—integral—derivative, PID, controller parameters configured to control the operation of a PID regulator comprised in the controller C or arranged separately to the controller C. The PID regulator may further be communicatively coupled to a selection of any of the controller C, the first controllable flow unit V and the second controllable flow unit P to control flow of the one or more additive gases AG1-AG2 or the flow of the one or more additive fluids AF1-AF2 to the bioreactor BR.

In a further example, the one model is generated using orthogonal partial least squares O-PLS analysis of a reference data set. A starting data set may be obtained by manually determining process properties/bioprocessing variables, or reference measurement results, for a particular bioprocess of a particular scale in a particular bioreactor of a particular size. The reference data set may then be obtained as the starting data set or by expanding the starting data set. Expanding the starting data set may e.g. be performed by increasing or decreasing the content or concentration of various components in the bioprocessing fluid FL, e.g. by spiking the bioprocessing fluid FL or diluting the bioprocessing fluid FL and obtaining measurement results of light reflection or absorption. This way, spectral measurement data over a range spanning outside normal biological range used in upstream cultivation can then be generated. A subset of the bioprocessing variables may be classified as wanted variables and another set may be classified as unwanted bioprocessing variables interfering with the wanted bioprocessing variables. Examples of a wanted variable may be any selection of any of glucose content, lactate content and viable cell density. An example of an unwanted variable may be gassing or additive gas flow rate/content, bioprocessing time, ambient air temperature and temperature of the bioprocessing fluid FL.

Expanding the starting data set may further be performed by systematically varying the unwanted bioprocessing variables in a systematic manner, e.g. by applying design of experience approach where variables such as concentrations, pH or temperature are systematically varied and spectroscopic data for the different variations are obtained.

Expanding the starting data set may further be performed by repeating the above mentioned steps for bioreactors having different volumes. The reference data set resulting from expanding the starting data set using any of the method above may further be analyzed using orthogonal partial least squares, O-PLS, analysis to filter away effects due to the bioreactor reactor scale/volume.

In other words, a model may be generated, using O-PLS, that receives input variables or measurement results and produces predicted variables/prediction parameters. The model is tuned/generated by providing reference measurement results as input variables and then adapting the model such that the output substantially matches reference predicted variables/prediction parameters of the reference data set.

In yet another wording, the O-PLS analysis identifies and separates systematic variation in input variables, e.g. measurement results in the form of a near infrared, NIR, spectra, that is not correlated to or orthogonal from the predictive variation in the predicted variables to the variation seen in the reference predicted variables. The result is a model with better predictive ability towards wanted bioprocessing variables and a simplification of the interpretation of the model.

O-PLS can be described as a generic preprocessing method for multivariate data. O-PLS analysis removes variation from input variables/descriptor variables X that is not correlated to predicted variables Y, e.g. glucose content. In mathematical terms this is equivalent to removing systematic variation in X that is orthogonal to Y. The non-correlated systematic variation in X is removed, making interpretation of the resulting PLS model easier and with the additional benefit that the non-correlated variation itself can be analyzed further.

The control parameters may further be generated/predicted based on the measurement results and wanted variables predicted by the one model.

In one example, the model predicts that glucose content is decreasing and is not maintained at a constant level by the current control parameters. An updated set of control parameters may then be generated by determining that the reduced glucose content predicted by the model indicates that a log phase has been entered by the bioprocess, and that increased proportional terms, e.g. of a proportional—integral—derivative PID controller, needs to be generated for the updated set of control parameters.

Figure 2:
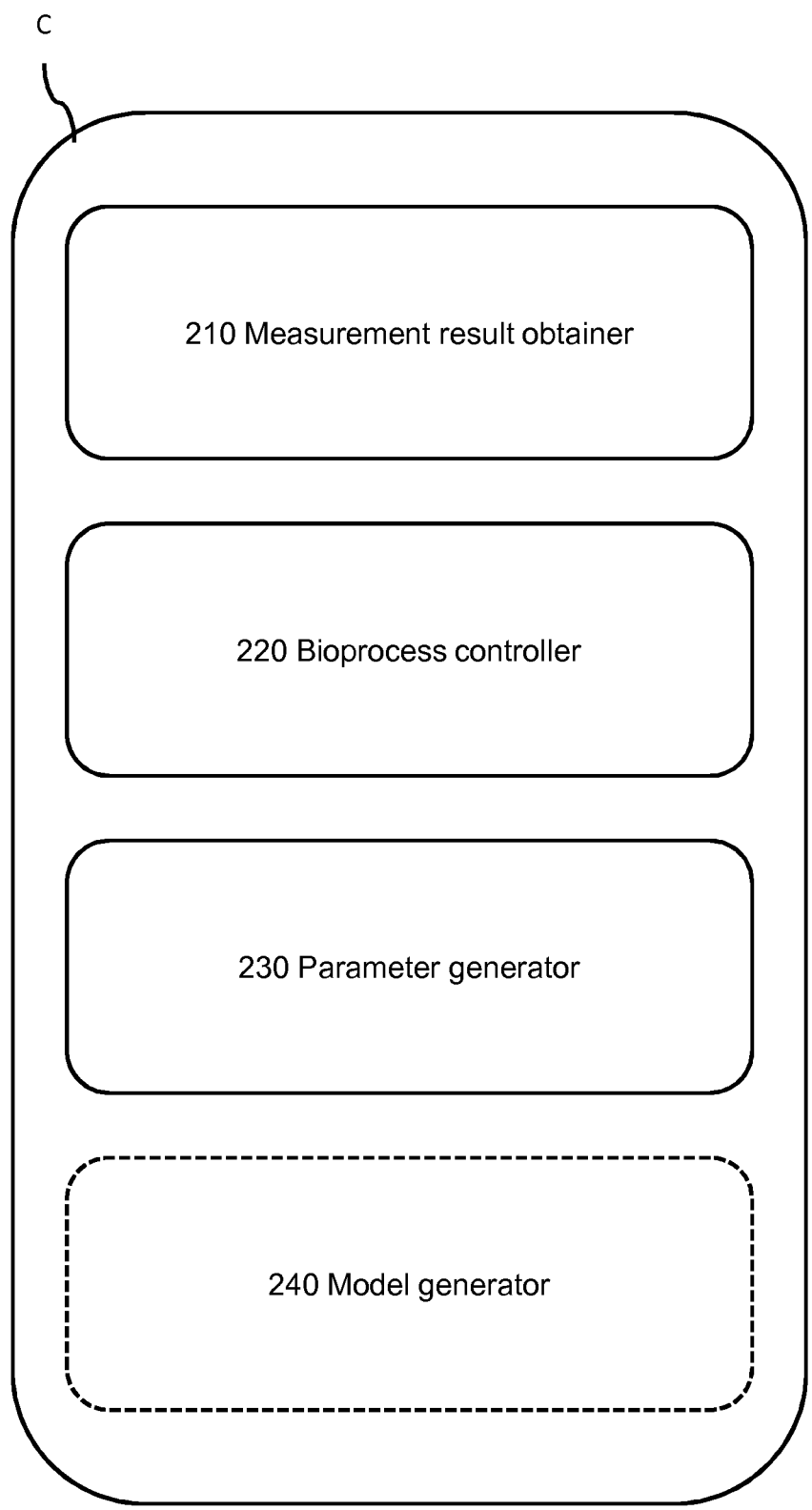
FIG. 2 illustrates functional modules of the controller according to one or more embodiments of the present disclosure.

FIG. 2 illustrates functional modules of the controller C according to one or more embodiments of the present disclosure. It is appreciated that the functionality of the controller C may be distributed over fewer or further functional modules depending on the application, and that the purpose of the concept of functional modules is used for illustrative purposes. In other words, the functionality of the controller may be concentrated to a single functional module or distributed over a plurality of functional modules without departing from the scope of the present disclosure.

In some embodiments, the controller C comprises a measurement result obtainer module 210. The measurement result obtainer module 210 is primarily configured to obtain measurement results by performing spectrophotometry of the bioprocessing fluid FL. The measurement results are typically obtained by receiving a control signal from the sensor S. The control signal typically comprises an indication of the measurement results resulting from performing spectrophotometry of the bioprocessing fluid FL, e.g. indicative of quantitative measurements of the reflection or transmission properties of the bioprocessing fluid FL as a function of wavelength of emitted light by the sensor S.

In one example, the measurement result comprises a generated spectrum of the bioprocess fluid, the spectrum showing the specific reflection/absorbance values of spectrum of light, e.g. a Near Infra-Red, NIR. In other words, reflection/absorbance values as a function of the wavelength of the emitted light. The reflection/absorbance values at specific wavelengths can be related to the molecular structures present in the bioprocess fluid and is accordingly indicative of the chemical composition of the fluid. The spectrum resulting from a full NIR scan may include a wavelength/wave number range between 4000-10000 $cm^{-1}$. If the wanted variable includes glucose content, the spectrum resulting from a NIR scan may preferably include a wavelength/wave number range between 5450-4497 $cm^{-1}$ and/or between 7501-5630 $cm^{-1}$. If the wanted variable includes Lactate content, the spectrum resulting from a NIR scan may preferably include a wavelength/wave number range between 8921-7146 $cm^{-1}$.

In some embodiments, the controller C comprises a bioprocess controller module 220. The bioprocess controller module 220 is typically configured to control a flow of one or more additive fluids AF1-AF2 and/or to control a flow of one or more additive gases AG1-AG2 to the bioreactor BR and/or the bioprocessing fluid FL of the bioreactor BR. The flow is typically controlled in response to values of wanted variables generated or predicted by the one model.

In one example, the controller C controls the flow of one or more additive gases AG1-AG2 to the bioreactor BR by sending a control signal to the first controllable flow unit V. The first controllable flow unit V typically comprises a valve unit and the control signal activates or controls one or more valves of the valve unit. E.g. the flow of oxygen into the bioprocessing fluid FL is controlled to a certain volume per time unit.

In one example, the controller C controls the flow of one or more additive fluids AF1-AF2 to the bioreactor BR by sending a control signal to the second controllable flow unit P. The second controllable flow unit P typically comprises a pump and the flow of the pump is controlled by the control signal. E.g. the flow of glucose into the bioprocessing fluid FL is controlled to a certain volume per time unit.

In one example, the controller C controls the flow of one or more additive gases AG1-AG2 and/or one or more additive fluids AF1-AF2 to the bioreactor BR by sending control parameters in the form of proportional—integral—derivative controller parameters to one or more PID controllers.

In some embodiments, the controller C comprises a parameter generator module 230. The parameter generator module 230 is typically configured to generate control parameters based on the measurement results of the sensor S and/or the one model. The control parameters typically reflect the responsiveness, of the bioprocess controller module 220 and/or one or more PID controllers external to the controller C controlling the flow of one or more additive gases AG1-AG2 and/or one or more additive fluids AF1-AF2 to the bioreactor BR, to changes in measurement result values, e.g. a decreased content of glucose in the bioprocessing fluid FL or density of viable cells in the bioprocessing fluid FL.

In one example, a change in reflection or transmission properties of the bioprocessing fluid FL indicated by the measurement results may indicate that the bioprocess is in a particular phase of the bioprocess, when the content of glucose in the bioprocessing fluid FL may drop rapidly, e.g. a log phase. The parameter generator module 230 may then generate control parameters providing a higher responsiveness to content of glucose. E.g. parameters indicating increased proportional terms of a PID controller.

In one example, a change in reflection or transmission properties of the bioprocessing fluid FL indicated by the measurement results may indicate that the bioprocess is in a particular phase of the bioprocess, when the content of glucose in the bioprocessing fluid FL is constantly offset, e.g. due to a residual error. The parameter generator module 230 may then generate control parameters providing a higher responsiveness to residual error. E.g. control parameters indicating increased integral terms of a PID controller.

In one example, a change in reflection and/or transmission properties of the bioprocessing fluid FL indicated by the measurement results may indicate that the bioprocess is in a particular phase of the bioprocess, when the content of glucose in the bioprocessing fluid FL is constantly offset, e.g. due to a residual error. The parameter generator module 230 may then generate control parameters providing a higher responsiveness to a rate of error change. E.g. parameters indicating increased derivative terms of a PID controller.

In some embodiments, the controller C comprises an optional model generator module 240. The model generator module 240 may generate the one model by performing orthogonal partial least squares analysis using a reference data set and/or a starting data set to, as further described in relation to FIG. 1, determine correlations between the wanted variables and extended reference measurement results, e.g. comprised in the reference data set and/or a starting data set, for a reference set of bioprocessing conditions.

A reference data set and/or a starting data set may be generated by proven methods in order to determine the reference value for various process parameters at various time points of the process. The proven methods may involve to measure reflection and/or transmission properties of the bioprocessing fluid FL as reference measurement results and simultaneously determine values of wanted variables of the bioprocess as reference predicted variables, e.g. determine a glucose content of the bioprocessing fluid FL. Parameters of particular interest for the model are considered as wanted parameters or parameters of interest to determine and/or control, but also parameters that might influence the spectrum recorded without being of interest to determine or control. An example of conventional methods performing multivariate data analysis, MVDA, employing unsupervised principal component analysis, PCA, and partial least squares regression methods, PLS, for prediction of multiple cultivation variables during bioprocess-monitoring can be found in "Chemometrics and in-line near infrared spectroscopic monitoring of a biopharmaceutical Chinese hamster ovary cell culture: prediction of multiple cultivation variables", Clavaud M, Roggo Y, Von Daeniken R, Liebler A, Schwabe J O, Talanta 26 Mar. 2013, 111:28-38.

The reference data set can then be transformed into a computer model by means of analyzing the absorbance as a function of wavelength and corresponding determined parameter values, e.g. indicative of process time point, and relating this absorbance to the parameter values determined by the proven methods. An example on how variables can be predicted using a model generated based on reference data can be found in "Designing a calibration set in spectral space for efficient development of an NIR method for tablet analysis", M Anik Alama, James Drennen III, Carl Anderson, Journal of Pharmaceutical and Biomedical Analysis Volume 145, 25 Oct. 2017, Pages 230-239.

In a further example, the one model is generated using orthogonal partial least squares analysis of the reference data set and/or the starting data set.

In one embodiment, the starting data set is expanded, e.g. by generating extended reference measurement results by extending measurement results and corresponding bioprocess variables values comprised in the starting data set.

Additionally or alternatively, expanding the starting data set may e.g. be performed by increasing or decreasing the content or concentration of various components in the bioprocessing fluid FL, e.g. by spiking the bioprocessing fluid FL or diluting the bioprocessing fluid FL. This way, spectral data over a range spanning outside normal biological range used in upstream cultivation can then be generated.

Increasing or decreasing the content or concentration may e.g. be performed via bench top experiments where the above described wanted parameters, such as glucose and/ or lactose/lactate content or viable cell density, are varied by e.g. spiking/dilution procedures in order to generate spectral data over a ranges spanning outside normal biological ranges, e.g. used in upstream cultivation.

Additionally or alternatively, expanding the starting data set may further be performed by systematically varying the unwanted bioprocessing variables in a systematic manner, e.g. by applying design of experience approach where variables such as glucose/lactose/lactate concentrations, pH or temperature are systematically varied and spectroscopic data for the different variations are obtained.

In one example, this can be performed by running experiments in suitable screening volume bioreactors and applying the systematically varied parameters/bioprocessing variables in a fashion as indicated by a design of experiments, DOE, set up. Optionally, and at the same time, the above described methodology may be applied for generating the model. A DOE setup typically involves varying the wanted and/or unwanted variables at particular step sizes within predetermined ranges.

Additionally or alternatively, expanding the starting data set may further be performed by repeating the above mentioned steps for bioreactors having different volumes.

This is preferentially performed by running the process of interest in a bioreactor with a volume larger than the volume of the screening bioreactor used to expand the starting data set e.g. in a volume same as the volume for the targeted process intended for a production situation, commonly between 50 and 2000 liters but can also be larger e.g. 10 000 liter, and/or at the same time applying the methodology described for generating the model.

The reference data set resulting from expanding the starting data set using any of the method above may further be analyzed using orthogonal partial least squares, O-PLS, analysis to filter away effects due to the bioreactor reactor scale/volume.

FIG. 3 shows the controller C according to one or more embodiments of the present disclosure. The controller C may be in the form of e.g. an Electronic Control unit, a server, an on-board control unit, a stationary computing device, a laptop control unit, a tablet control unit, a handheld control unit, a wrist-worn control unit, a smart watch, a smartphone or a smart TV. The controller C may comprise processing circuitry 312 communicatively coupled to a communications interface, e.g. a transceiver 304, configured for wired or wireless communication. The controller C may further comprise at least one optional antenna (not shown in the figure). The antenna may be coupled to the transceiver 304 and is configured to transmit and/or emit and/or receive wired or wireless signals in a communication network, such as WiFi, Bluetooth, 3G, 4G, and 5G etc. In one example, the processing circuitry 312 may be any of a selection of a processor and/or a central processing unit and/or processor modules and/or multiple processors configured to cooperate with each-other. Further, the controller C may further comprise a memory 315 communicatively coupled to the processing circuitry 312. The memory 315 may e.g. comprise a selection of a hard RAM, disk drive, a floppy disk drive, a flash drive or other removable or fixed media drive or any other suitable memory known in the art. The memory 315 may contain instructions executable by the processing circuitry to perform any of the steps or methods described herein. The processing circuitry 312 may be communicatively coupled to a selection of any of the transceiver 304 and the memory 315. The controller C may be configured to send/receive control signals directly to/from any of the above mentioned units or to external nodes or to send/receive control signals via a wired and/or wireless communications network.

The wired/wireless transceiver 304 and/or a wired/wireless communications interface may be configured to send and/or receive data values or parameters as a signal to or from the processing circuitry 312 to or from other external nodes.

In an embodiment, the transceiver 304 communicates directly to external nodes/units or via the wireless communications network. In one example, control parameters are sent to an external PID controller.

In one or more embodiments the controller C may further comprise an input device 317, configured to receive input or indications from a user and send a user input signal indicative of the user input or indications to the processing circuitry 312.

In one or more embodiments the controller C may further comprise a display 318 configured to receive a display signal indicative of rendered objects, such as text or graphical user input objects, from the processing circuitry 312 and to display the received signal as objects, such as text or graphical user input objects.

In one embodiment the display 318 is integrated with the user input device 317 and is configured to receive a display signal indicative of rendered objects, such as text or graphical user input objects, from the processing circuitry 312 and to display the received signal as objects, such as text or graphical user input objects, and/or configured to receive input or indications from a user and send a user-input signal indicative of the user input or indications to the processing circuitry 312.

In a further embodiment, the controller C may further comprise and/or be coupled to one or more additional sensors (not shown in the figure) configured to receive and/or obtain and/or measure physical properties pertaining to the bioprocessing system SYS and send one or more sensor signals indicative of the physical properties to the processing circuitry 312. An example of such an additional sensor may be an ambient air pressure sensor configured to measure the ambient air pressure where the bioprocessing system SYS is located.

In one or more embodiments, the processing circuitry 312 is further communicatively coupled to the input device 317 and/or the display 318 and/or the additional sensors.

In embodiments, the communications network communicate using wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the controller C may comprise the necessary communication capabilities in the form of e.g., functions, means, units, elements, etc., for performing the present solution. Examples of other such means, units, elements and functions are: processors, memory, buffers, control logic, encoders, decoders, mapping units, multipliers, decision units, selecting units, switches, modulators, demodulators, inputs, outputs, antennas, amplifiers, receiver units, transmitter units, DSPs, power supply units, power feeders, communication interfaces, communication protocols, etc. which are suitably arranged together for performing the present solution.

Especially, the processing circuitry of the present disclosure may comprise one or more instances of a processor, processor modules and multiple processors configured to cooperate with eachother, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processing circuitry" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as call processing control, user interface control, or the like.

Figure 4:
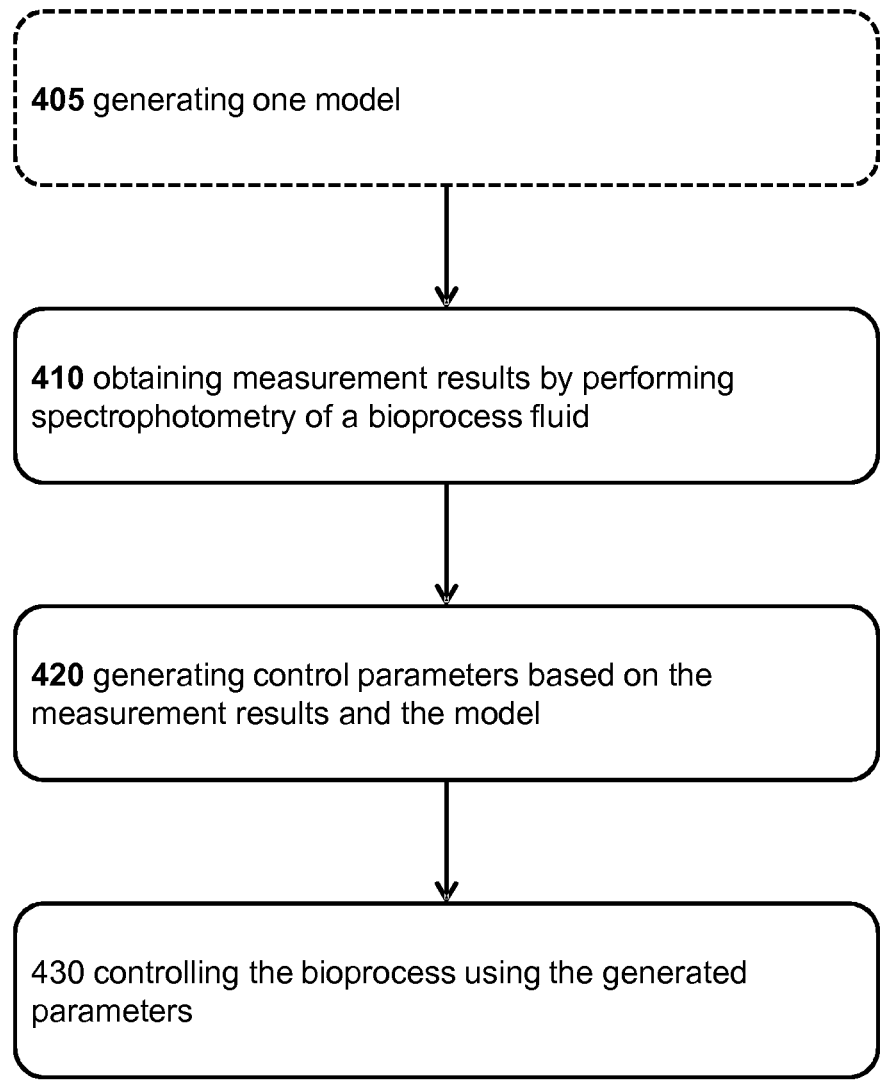
FIG. 4 shows a flowchart of a method according to one or more embodiments of the present disclosure.

FIG. 4 shows a flowchart of a method 400 according to one or more embodiments of the present disclosure. A computer implemented method 400 is provided and performed by a controller C configured to control a bioprocess comprised in a bioreactor BR. The method comprises:

Step 410: obtaining measurement results by performing spectrophotometry of a bioprocessing fluid FL. The measurement results are typically obtained by receiving a control signal from the sensor S. The control signal being indicative of the measurement results, e.g. reflection or transmission properties of the bioprocessing fluid FL as a function of wavelength, as further described in relation to FIG. 2.

In one example, the bioprocess is a cell cultivation process and the measurement results are indicative of transmission properties of the bioprocessing fluid FL as a function of wavelength, e.g. intensity of near infrared light, NIR, as a function of wavelength. The wavelengths of the NIR light may typically be comprised in a range of 780 nm to 2500 nm.

Step 420: generating control parameters based on the measurement results and one (single) model.

The control parameters typically reflect the responsiveness, of the bioprocess controller module 220 and/or one or more PID controllers external to the controller C controlling the flow of one or more additive gases AG1-AG2 and/or one or more additive fluids AF1-AF2 to the bioreactor BR, to changes in measurement result values, e.g. a decreased content of glucose in the bioprocessing fluid FL or density of viable cells in the bioprocessing fluid FL. Further details and examples of generating control parameters are further described in relation to FIG. 2.

Alternatively or additionally, in one embodiment the step of generating the control parameters further comprises estimating/predicting a set of wanted bioprocessing variables as output from the model by providing the obtained measurement results to the model. Alternatively or additionally, the generated control parameters may further be based on the estimated/predicted set of wanted bioprocessing variables. In one example, the estimated/predicted set of wanted bioprocessing variables indicates that the bioprocess has entered a different phase and control parameters are selected from a predefined set of parameters associated to that particular phase, e.g. a log phase of cell cultivation.

Alternatively or additionally, the control parameters are further based on a processing time of the bioprocess. The step of generating the control parameters then further comprises mapping the set of wanted bioprocessing variables and/or processing time to a phase of a plurality of phases of the bioprocess. Alternatively or additionally, the generated control parameters further depends on the mapped phase.

Alternatively or additionally, the generated control parameters comprise proportional—integral—derivative controller parameters. E.g. a selection of any of proportional, integral, and derivative terms of a PID controller.

Step 430: controlling the bioprocess using the generated parameters. Controlling the bioprocess may typically comprise controlling the flow of one or more additive gases AG1-AG2 and/or one or more additive fluids AF1-AF2 to the bioreactor BR. Controlling the bioprocess is further described in relation to FIG. 2.

An example of an execution of the above described method can be found in relation to FIG. 1. Further details and examples of the method can, as mentioned, be found in relation to FIG. 2 detailing the functionality of the controller C.

Alternatively or additionally, in one embodiment the wanted bioprocessing variables are indicative of a selection of any of glucose content, lactose/lactate content and viable cell content of the bioprocessing fluid FL.

Alternatively or additionally, in one embodiment the bioprocess comprises performing cell cultivation.

Alternatively or additionally, in one embodiment, the method 400 further comprises the step of generating 405 the model. Alternatively or additionally, in one embodiment generating the model further comprises performing orthogonal partial least squares, O-PLS, analysis using a reference data set to determine correlations between reference wanted variables/predicted variables and extended reference measurement results for a reference set of bioprocessing conditions.

Alternatively or additionally, the step of generating 405 the model further comprises any selection of the steps of identifying bioprocessing variables making a contribution to a set of reference measurement results, classifying the bioprocessing variables as either wanted variables or unwanted variables, generate extended reference measurement results for an extended set of bioprocessing conditions, determining correlations between wanted variables and the extended reference measurement results for a reference set of bioprocessing conditions and generating the one model based on the determined correlations.

Alternatively or additionally, in one embodiment, the step of controlling the bioprocess 430 further comprises controlling a flow of one or more additive fluids AF1-AF2. Controlling the flow may comprise controlling the flow of a pump providing additive fluids to the bioreactor BR, as further described in relation to FIG. 2.

Alternatively or additionally, in one embodiment, the step of controlling the bioprocess 430 further comprises controlling a flow of one or more additive gases AG1-AG2. Controlling the flow may comprise controlling the flow of a pump providing additive fluids to the bioreactor BR, as further described in relation to FIG. 2.

In one embodiment, a controller C is provided, the controller comprises processing circuitry 312 and a memory 315. The memory 315 containing instructions executable by said processor 312, whereby said controller is operative to perform any of the method steps according the method 400.

In one embodiment, a bioprocessing system SYS is provided comprising a sensor S configured to perform spectrophotometry of a bioprocessing fluid FL and provide measurement results comprised in a control signal, a first controllable flow unit V configured to control a flow of one or more additive gases AG1-AG2 to a bioreactor BR in response to control signals, a second controllable flow unit P configured to control a flow of one or more additive fluids AF1-AF2 to a bioreactor BR in response to control signals., Alternatively or additionally, in one embodiment, the controller C is further configured to receive/send control signals to/from the sensor S, the first controllable flow unit V and the second controllable flow unit P.

Alternatively or additionally, in one embodiment, a computer program is provided and comprises computer-executable instructions for causing a controller C, when the computer-executable instructions are executed on processing circuitry 312 comprised in the controller C, to perform any of the method steps described herein.

Alternatively or additionally, in one embodiment, a computer program product is provided and comprising a computer-readable storage medium, the computer-readable storage medium having the computer program above embodied therein.

Finally, it should be understood that the invention is not limited to the embodiments described above, but also relates to and incorporates all embodiments within the scope of the appended independent claims.

The invention claimed is:

1. A computer implemented method performed by a controller configured to control a bioprocess comprised in a bioreactor, the method comprising:
    identifying a set of bioprocessing variables making a contribution to a set of reference measurement results,
    classifying a first subset of the set of bioprocessing variables as wanted bioprocessing variables,
    classifying a second subset of the set of bioprocessing variables as unwanted bioprocessing variables,
    obtaining measurement results by performing spectrophotometry of a bioprocessing fluid,
    generating control parameters based on the measurement results and one model, wherein the control parameters are further based on a processing time of the bioprocess and the step of generating the control parameters further comprises:
        estimating a set of wanted bioprocessing variables as output from the one model by providing the obtained measurement results to the one model,
        wherein the generated control parameters are further based on the estimated set of wanted bioprocessing variables,
        mapping the processing time to a phase of a plurality of phases of the bioprocess, and,
        wherein the generated control parameters further depend on the mapped phase,
        wherein the generated control parameters specifies an allowable amount of the unwanted bioprocessing variables, and
    controlling the bioprocess using the generated control parameters.

2. The method according to claim 1, wherein the control parameters are generated based on the measurement results and a single model.

3. The method according to claim 1, wherein the generated control parameters comprises proportional-integral-derivative controller parameters.

4. The method according to claim 1, wherein:
    the wanted bioprocessing variables are indicative of a selection of any of glucose content, lactose content and viable cell content of the bioprocessing fluid (FL); and
    the unwanted bioprocessing variables are indicative of a selection of any of gassing or additive gas flow rate/content, bioprocessing time, ambient air temperature and temperature of the bioprocessing fluid.

5. The method according to claim 1, wherein the bioprocess comprises cell cultivation.

6. The method according to claim 5, wherein the bioprocess comprises at least two of a lag phase, a log phase or a stationary phase.

7. The method according to claim 1, the method further comprising generating the one model by at least systematically varying the unwanted bioprocessing variables.

8. The method according to claim 7, wherein generating the one model further comprises performing orthogonal partial least squares analysis using a reference data set to determine correlations between the wanted bioprocessing variables and extended reference measurement results for a reference set of bioprocessing conditions.

9. The method according to claim 7, further comprising:
    generate extended reference measurement results for an extended set of bioprocessing conditions,
    determining correlations between wanted variables and the extended reference measurement results for a reference set of bioprocessing conditions, generating the one model based on the determined correlations.

10. The method according to claim 1, wherein controlling the bioprocess further comprises controlling a flow of one or more additive fluids.

11. The method according to claim 1, wherein controlling the bioprocess further comprises controlling a flow of one or more additive gases.

12. A controller, the controller comprising:
    processing circuitry; and
    a memory, said memory containing instructions executable by said processor, whereby said controller is operative to perform the method steps according to claim 1.

13. A bioprocessing system comprising:
    a sensor configured to perform spectrophotometry of a bioprocessing fluid and provide measurement results comprised in a control signal, a first controllable flow unit configured to control a flow of one or more additive gases to a bioreactor in response to control signals, a second controllable flow unit configured to control a flow of one or more additive fluids to a bioreactor in response to control signals, and the controller according to claim 12 further configured to receive/send control signals to/from the sensor, the first controllable flow unit and the second controllable flow unit.

14. A computer program comprising computer-executable instructions for causing a controller, when the computer-executable instructions are executed on processing circuitry comprised in the controller, to perform the method steps according to claim 1.

15. A computer program product comprising a computer-readable storage medium, the computer-readable storage medium having the computer program according to claim 14 embodied therein.

\* \* \* \* \*